US00PP09034P

United States Patent [19]

Layng

[11] Patent Number: Plant 9,034

[45] Date of Patent: Jan. 3, 1995

[54] CHRYSANTHEMUM PLANT NAMED ROSEPINK DEBONAIR

[76] Inventor: W. John Layng, 10311 Mountington Ct., Vienna, Va. 22182

[21] Appl. No.: 203,318

[22] Filed: Mar. 1, 1994

[51] Int. Cl.[6] ..... A01H 5/00

[52] U.S. Cl. ..... Plt./80

[58] Field of Search ..... Plt. 76, 80, 81

*Primary Examiner*—Howard J. Locker

*Attorney, Agent, or Firm*—Foley & Lardner

[57] ABSTRACT

A Chrysanthemum plant named Rosepink Debonair particularly characterized by its flat capitulum form; decorative capitulum type; rose-pink ray floret color; diameter across face of capitulum of 64 to 70 mm when fully opened; spreading branching pattern, with 6 to 8 breaks after pinch when grown outside under natural daylength in fall flowerings, and 5 to 7 breaks when grown in 10 cm pots for spring flowerings; natural season flower date of August 23 to 31 when planting rooted cuttings on June 21 to 25 in Salinas, Calif., and September 15 to 30 when planting rooted cuttings June 11 to June 18 in Hightstown, N.J.; flowering response of 49 to 53 days after rooting in no light/no shade programs in spring in Salinas; plant height of 30 to 38 cm when grown in fall under natural daylength with no growth regulators in New Jersey, and 15 to 20 cm when grown in 10 cm pots in spring with no growth regulator applications; and durable, uniform performance.

1 Drawing Sheet

1

The present invention comprises a new and distant cultivar of Chrysanthemum, botanical known as *Dendranthema grandiflora,* and referred to by the cultivar name Rosepink Debonair.

Rosepink Debonair, identified as 8906 (91-#02031), is a spontaneous mutation of the cultivar Debonair, disclosed in U.S. Plant Pat. No. 5,324, and was selected to expand the color range of the parental variety.

Rosepink Debonair was discovered and selected by W. John Layng as one flowering plant within a flowering block of Debonair in September 1990, in a controlled environment in McLean, Va.

The first act of asexual reproduction of Rosepink Debonair was accomplished when vegetative cuttings were taken from the initial selection in March 1991 in a controlled environment in McLean, Va., by technicians working under supervision of W. John Layng.

Horticultural examination of controlled flowerings of successive plantings has shown that the unique combination of characteristics as herein disclosed for Rosepink Debonair are firmly fixed and are retained through successive generations of asexual reproduction.

Rosepink Debonair has not been observed under all possible environmental conditions. The phenotype may vary significantly with variations in environment such as temperature, light intensity and daylength without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Rosepink Debonair, which, in combination, distinguish this Chrysanthemum as a new and distinct cultivar:

1. Flat capitulum form.

2

2. Decorative capitulum type.
3. Rose-pink ray floret color.
4. Diameter across face of capitulum of 64 to 70 mm when fully opened.
5. Branching pattern is spreading, with 6 to 8 breaks after pinch when grown outside under natural daylength in fall flowerings, and 5 to 7 breaks when grown in 10 cm pots for spring flowerings.
6. Natural season flower date of August 23 to 31 when planting rooted cuttings on June 21 to 25 in Salinas, Calif., and September 15 to 30 when planting rooted cuttings June 11 to June 18 in Hightstown, N.J.
7. FLowering response of 49 to 53 days after rooting in no light/no shade programs in spring in Salinas.
8. Plant height of 30 to 38 cm when grown in fall under natural daylength with no growth regulators in New Jersey, and 15 to 20 cm when grown in 10 cm pots in spring with no growth regulator applications.
9. Durable, uniform performance.

The accompanying photographic drawing is a color photograph of Rosepink Debonair grown as a small potted Chrysanthemum in the spring in a 10 cm pot, with the colors being as nearly true as possible with illustrations of this type.

Of the commercial cultivars known to the inventor, the most similar in comparison to Rosepink Debonair is the parent cultivar Debonair. All traits of Rosepink Debonair are similar to those of Debonair, except for the ray floret color. The ray floret color of Rosepink Debonair is described as rose-pink, while the ray floret color of Debonair is described as purple.

In the following description, color references are made to The Royal Horticultural Society Colour Chart. The color values were determined on plant material grown as a pinched garden mum grown outdoors in Salinas, Calif. on Aug. 16, 1993.

Classification:

*Botanical.*—*Dendranthema grandiflora* cv Rosepink Debonair.

*Commercial.*—Flat decorative spray pot mum and garden mum.

INFLORESCENCE

A. Capitulum:
*Form.*—Flat.
*Type.*—Decorative.
*Diameter across face.*—64 to 70 mm when fully opened.

B. Corolla of ray florets:
*Color (general tonality from a distance of three meters).*—Rose-pink.
*Color (upper surface).*—74C to 74D.
*Color (under surface).* —74D.
*Shape.*—Straight, some outer ray florets spooned, cross section concave.

C. Corolla of disc florets:
*Color (mature).*—14A.
*Color (immature).*—14A tinged with 144C.

D. Reproductive organs:
*Androecium.*—Present on disc florets only; very few disc florets, scant pollen.
*Gynoecium.*—Present on both ray and disc florets.

PLANT

A. General appearance:
*Height.*—30 to 38 cm when grown in fall under natural daylength with no growth regulators in New Jersey, and 15 to 20 cm when grown in 10 cm pots in spring with no growth regulator applications.
*Branching pattern.*—Spreading, with 6 to 8 breaks after pinch when grown outside under natural daylength in fall flowerings and with 5 to 7 breaks when grown in 10 cm pots for spring flowerings.

B. Foliage:
*Color (upper surface).*—147A.
*Color (under surface).*—147B.
*Shape.*—Lobed, slightly serrated.

I claim:

1. A new and distinct Chrysanthemum plant named Rosepink Debonair, as described and illustrated.

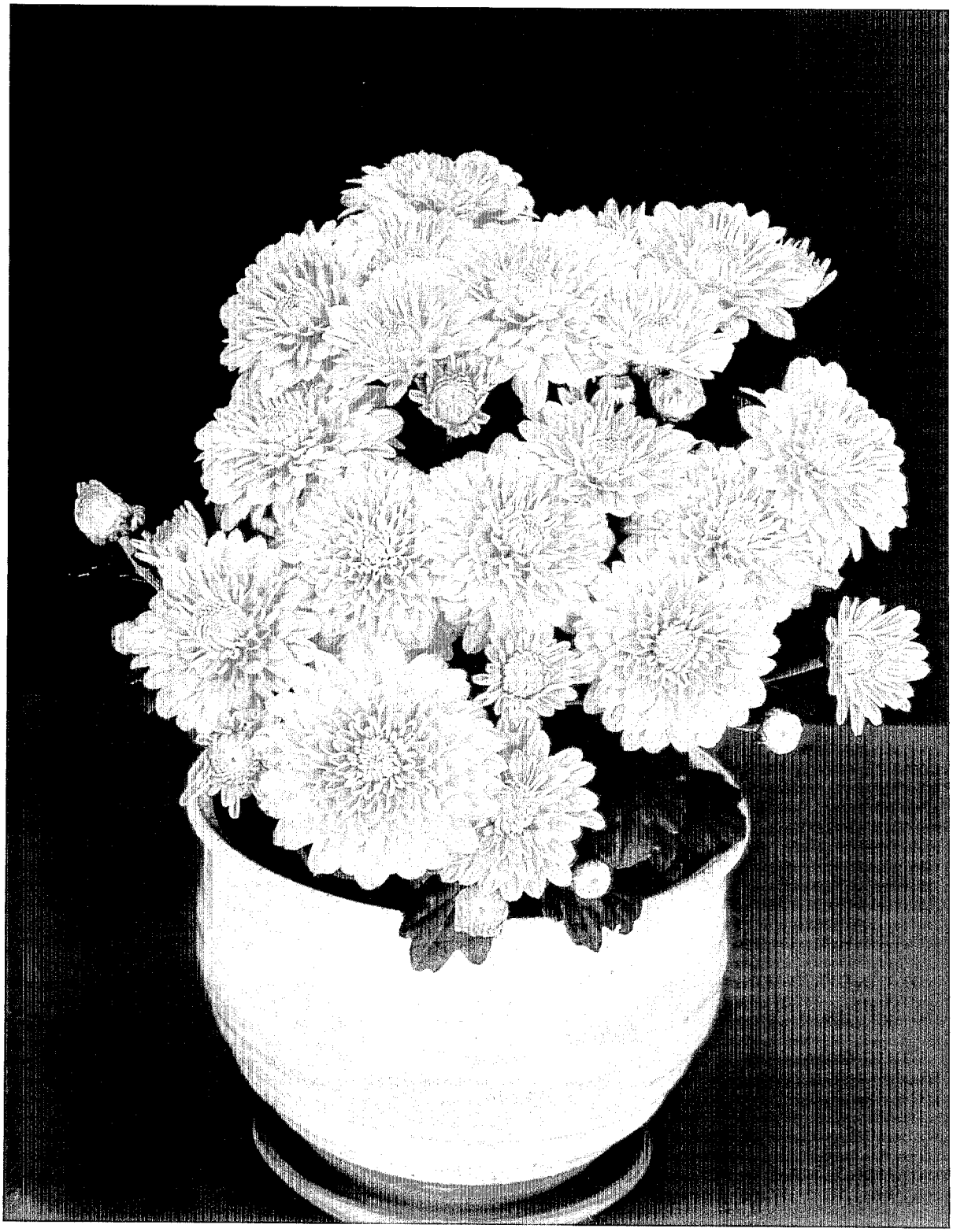

* * * * *